United States Patent [19]

Braughler et al.

[11] Patent Number: 4,771,042
[45] Date of Patent: Sep. 13, 1988

[54] INHIBITION OF ANGIOGENESIS INVOLVING THE COADMINISTRATION OF STEROIDS WITH HEPARIN OR HEPARIN FRAGMENTS

[75] Inventors: John M. Braughler; Edward D. Hall, both of Portage; John M. McCall, Kalamazoo; Wendell Wierenga, Oshtemo Township, Kalamazoo County, Mich.; Judah Folkman, Brookline, Mass.

[73] Assignee: The Upjohn Company, Kalamazoo, Mich.

[21] Appl. No.: 822,111

[22] Filed: Jan. 24, 1986
(Under 37 CFR 1.47)

Related U.S. Application Data

[63] Continuation of Ser. No. 801,532, Nov. 25, 1985, abandoned, which is a continuation of Ser. No. 781,100, Sep. 27, 1985, abandoned.

[51] Int. Cl.$^4$ .................. A61K 31/56; A61K 31/58
[52] U.S. Cl. .................... 514/171; 514/177; 514/178; 514/179; 514/180; 514/181; 514/172
[58] Field of Search ............... 514/177, 178, 179, 180, 514/181, 171, 172

[56] References Cited

FOREIGN PATENT DOCUMENTS 0114589 6/1984 European Pat. Off. ............... 31/725

OTHER PUBLICATIONS

Folkman, Jr., Proceedings of AACR 26 (Mar. 1985), 384–385.
Folkman, J., et al., Science 221 (Aug. 19, 1983), 719–725.

*Primary Examiner*—Leonard Schenkman
*Assistant Examiner*—Joseph A. Lipovsky
*Attorney, Agent, or Firm*—Ruth Hattan Newtson

[57] ABSTRACT

A method of inhibiting angiogenesis in a warm blooded animal which comprises administering to said animal an anti-angiogenic effective amount of a compound of the formula:

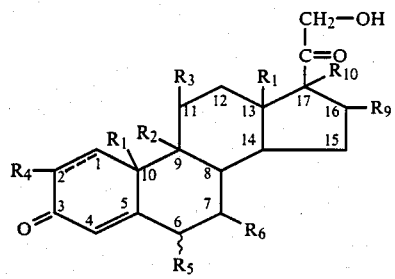

wherein the dotted line between positions C-1 and C-2 means the presence or absence of a double bond; the ~bond at C-6 denotes $\alpha$ or $\beta$;
wherein $R_1$ is $CH_3$ or $-C_2H_5$;
wherein $R_2$ is H, and $R_3$ is in the $\alpha$-position and is —OH, —O-alkyl($C_1$-$C_{12}$), —OC(=O)alkyl($C_1$-$C_{12}$), —OC(=O)aryl, —OC(=O)N(R)$_2$, or —OC(=O)OR$_7$, wherein aryl is furyl, thienyl, pyrrolyl, or pyridyl wherein each of said hetero moiety is optionally substituted with one or two ($C_1$-$C_4$)-alkyl groups or aryl is —(CH$_2$)$_f$-phenyl wherein f is 0 to 2 and wherein the phenyl ring is optionally substituted with one to three groups selected from chlorine, fluorine, bromine, alkyl($C_1$-$C_3$), alkoxy($C_1$-$C_3$), thioalkoxy($C_1$-$C_3$), Cl$_3$C—, F$_3$C—, —NH$_2$ and —NHCOCH$_3$ and wherein R is hydrogen, alkyl($C_1$-$C_4$), or phenyl and each R can be the same or different;
and wherein $R_7$ is aryl as herein defined or alkyl($C_1$-$C_{12}$); or
wherein $R_2$ is $\alpha$-Cl and $R_3$ is $\beta$-Cl; or
wherein $R_2$ and $R_3$ taken together are oxygen (—O—) bridging positions C-9 and C-11; or
wherein $R_2$ and $R_3$ taken together form a double bond between positions C-9 and C-11;
wherein $R_4$ is H, CH$_3$, Cl or F;
wherein $R_5$ is H, OH, F, Cl, Br, CH$_3$, phenyl, vinyl or allyl;
wherein $R_6$ is H or CH$_3$;
wherein $R_9$ is H, OH, CH$_3$, F or =CH$_2$; and
wherein $R_{10}$ is H, OH, CH$_3$ or $R_{10}$ forms a second bond between positions C-16 and C-17.

9 Claims, No Drawings

INHIBITION OF ANGIOGENESIS INVOLVING THE COADMINISTRATION OF STEROIDS WITH HEPARIN OR HEPARIN FRAGMENTS

CROSS REFERENCE TO RELATED APPLICATIONS

This application is a continuation of application U.S. Ser. No. 801,532, filed Nov. 25, 1985, now abandoned, which is a continuation of application U.S. Ser. No. 781,100, filed Sept. 27, 1985, now abandoned.

BACKGROUND OF THE INVENTION

Angiogenesis is the development of blood vessels which typically would lead to a vascular bed capable of sustaining viable tissue. Angiogenesis is a necessary process in the establishment of embryonic tissue and development of a viable embryo. Similarly angiogenesis is a necessary step in the establishment and development of tumor tissue as well as certain inflammatory conditions. The inhibition of angiogenesis obviously could be useful in the control of embryogenesis, inflammatory conditions, and tumor growth, as well as numerous other conditions as set forth in more detail hereinafter.

Co-pending application Ser. No. 701,601 filed Feb. 14, 1985 describes a novel class of solution stable non-glucocorticoid steroids which are useful in the inhibition of angiogenesis.

European application No. 83870132.4 (Publication No. 0 114 589) published Aug. 1, 1984, describes the use of cortisone, hydrocortisone and 11α-hydrocortisone in combination with heparin in the inhibition of angiogenesis.

J. Folkman, et al., Science 221, 719–725 (1983), further describes the angiogenesis inhibitory effects of heparin and heparin fragments in combination with cortisone. Folkman further elaborates on the use of heparin or heparin fragments in combination with hydrocortisone in the Proceedings of AACR 26, 384–385 (March 1985).

FIELD OF INVENTION

The present invention is a method of using non-glucocorticoid steroids and heparin or heparin fragments to inhibit angiogenesis.

SUMMARY OF INVENTION

The method of the present invention utilizes steroids of general Formula I (see Formula Chart) wherein the various substituents have the following meanings:
  the dotted line between positions C-1 and C-2 means the presence or absence of a second or double bond;
  $R_1$ is $CH_3$ or $C_2H_5$;
  $R_2$ is H and $R_3$ is in the α-position is —OH, —O-alkyl($C_1$-$C_{12}$), —O-COalkyl($C_1$-$C_{12}$), —O-COaryl, —O-CON(R)$_2$, or OCOOR$_7$ wherein aryl is phenyl wherein f is 0 to 2 and wherein the phenyl ring is —(CH$_2$)$_f$— optionally substituted with from 1 to 3 groups selected from Cl, F, Br, alkyl($C_1$-$C_3$), alkoxy($C_1$-$C_3$), thioalkoxy($C_1$-$C_3$), i.e., —S-alkyl(-$C_1$-$C_3$), Cl$_3$C—, F$_3$C, NH$_2$, or —NHCOCH$_3$, i.e., acetamido, or aryl is furyl, thienyl, pyrrolyl or pyridyl each of said hetero moiety being optionally substituted with one or two $C_1$-$C_4$ alkyl groups, and wherein R is hydrogen, alkyl($C_1$-$C_4$), or phenyl and each R can be the same or different; wherein $R_7$ is aryl as defined or alkyl($C_1$-$C_{12}$); or
  $R_2$ is α-Cl and $R_3$ is β-Cl; or
  $R_2$ and $R_3$ taken together form an oxygen (—O—) bridging positions C-9 and C-11; or
  $R_2$ and $R_3$ taken together form a second or a double bond between positions C-9 and C-11;
  $R_4$ is H, $CH_3$, Cl or F;
  $R_5$ is H, OH, F, Cl, Br, $CH_3$, phenyl, vinyl or allyl;
  $R_6$ is H or $CH_3$;
  $R_9$ is H, OH, $CH_3$, F or $=CH_2$; and
  $R_{10}$ is H, OH, $CH_3$ or $R_{10}$ forms a second or double bond between positions C-16 and C-17.

The present invention provides a method of inhibiting angiogenesis in a warm blooded animal and more preferably in a mammal which comprises administering to said warm blooded animal a steroid of Formula I optionally with heparin or a heparin fragment.

DETAILED DESCRIPTION OF INVENTION

Preferred embodiments of the present invention are the administration of a steroid as represented by Formulas II to VI wherein the substituent groups have the following meanings:

In Formulas II to VI each of $R_4$, $R_7$ and $R_8$ is hydrogen; $R_1$ is alkyl($C_1$-$C_3$), preferably $CH_3$ or $C_2H_5$; $R_5$ is $CH_3$, F, Cl, Br, H or OH, and more preferably $R_5$ is in the α-position and is $CH_3$, H or F; $R_6$ is H or $CH_3$ and more preferably is H; $R_9$ is H, α-OH or $CH_3$; and $R_{10}$ is α-H or α-OH. Additionally in Formula III $R_2$ is hydrogen and $R_3$ is in the α-position and is OH, —O-alkyl(-$C_1$-$C_{12}$), preferably —O-alkyl($C_1$-$C_4$), —O-COalkyl(-$C_1$-$C_{12}$), preferably —O-COalkyl($C_1$-$C_6$), —O-COaryl, —O-CON(R)$_2$ or —OCOOR$_7$ wherein aryl, R, and $R_7$ have the meanings defined in Formula I and preferably aryl is phenyl and R is hydrogen or methyl. In practicing the present invention the steroids of Formula I can be administered alone or in combination with heparin or a heparin fragment.

The aryl moiety in the $R_3$ group —OCOaryl is attached to the carbonyloxy moiety through any of the available ring carbon atoms of said aryl moiety.

Any reference herein to compounds of Formula I includes pharmacologically acceptable salts thereof.

The compounds of the present invention are useful in treating the following diseases and injuries: head trauma, spinal trauma, septic or traumatic shock, stroke, and hemorrhagic shock. In addition utility in cancer as well as other disorders or physiological phenomenon dependent on angiogenesis such as embryo implantation (antifertility), arthritis, and atherosclerosis is exhibited with these compounds coadministered with oral heparin or systemic heparin fragments (see J. Folkman, et al., Science 221, 719–725 (1983). The compounds of the present invention possess substantially none of the typical steroid glucocorticoid effects.

The steroids of Formula I can be administered orally, intramuscularly, intravenously and by suppository, and the effective dosage range is 10 to 750 mg/kg/day. Additionally, a dosage regimen of using a loading dose of about 30 mg/kg followed by a repetitive as needed maintenance dose of about 15 mg/kg may be desirable. The compounds of the present invention may be coadministered with low doses of glucocorticoids. For the treatment of cancer including head tumors and other conditions dependent upon angiogenesis a preferred dosage range of a compound of Formula I is 10 to 500 mg/kg/day for 30 days repeated for 30 additional days after a 30 day respite or on a chronic intermittent basis such as every other day therapy until tumor regression or absence of metastases is observed. The preferred route of administration is orally, by suppository or intramuscularly. For the treatment of arthritis the preferred dosage range of a compound of Formula I is 10 to 250 mg/kg/day or every other day until absence or significant reduction in associated symptoms is observed. For the treatment of atherosclerosis the preferred dosage range of a compound of Formula I is 10 to 250 mg/kg/day or every other day chronically. And, for the disruption of or prevention of embryo implantation the preferred dosage range of a compound of Formula I is 10 to 250 mg/kg/day chronically to fertile women. When coadministering a compound of Formula I with heparin or a heparin fragment in practicing the present invention the amount of heparin or heparin to be utilized varies from 1,000 to 50,000 Units/kg/day with heparin being administered orally and heparin fragments being administered subcutaneously, intramuscularly or intravenously.

The utility of the compounds of the present invention can be demonstrated in various test models as follows: For head trauma, mice are struck on the head with a standard weight which is dropped from a set height. They are then dosed subcutaneously with the test compound. After one hour the motor abilities of the mice are assessed. Active test compounds promote improved motor activity relative to controls. For spinal trauma, see E. D. Hall and J. M. Braughler, Surg. Neurol. 18, 320-327 (1982) and J. Neurosurg. 56, 838-844 (1982). Septic (traumatic) shock is demonstrated in a rat model whereby test compound is administered and protection of the rats from the lethal effects of endotoxin is measured. For stroke, the carotid arteries of gerbils are ligated for a brief period after which test compound is administered subcutaneously. The behavior of the gerbils is observed after a recovery period, and gerbils receiving test compound display a more normal behavior after the recovery period. And for hemorrhagic shock, by published procedures used to evaluate glucocorticoids. The inhibition of angiogenesis associated with tumor formation and proliferation is typically evaluated in the chick embryo or rabbit cornea, e.g., as reported by J. Folkman, et al., Science 221, 719-725 (1983). Illustratively the compound of Formula I wherein $R_2$ and $R_3$ form a double bond between positions 9 and 11, $R_1$ is $CH_3$, $R_4$ is H, $R_5$ is $\alpha$-F, $R_6$ is H, $R_9$ is $\beta$-$CH_3$ and $R_{10}$ is $\alpha$-OH, i.e., 6$\alpha$-fluoro-17$\alpha$-hydroxy-21-hydroxy-16$\beta$-methylpregna-4,9(11)-diene-3,20-dione when administered alone at a dosage of 90 μg per cc of polymeric vehicle in the rabbit cornea tumor test model inhibited angiogenesis by 60% of control and when coadministered with 18 μg per cc of polymeric vehicle of a hexasaccharide fragment of heparin the percent inhibition of angiogenesis increased to 80% of control. Control in each instance was polymeric vehicle alone.

Sterile aqueous solutions of the compounds of Formula I typically will contain other components such as preservatives, anti-oxidants, chelating agents, or other stabilizers. Suitable preservatives can include benzyl alcohol, the parabens, benzalkonium chloride, or benzoic acid. Anti-oxidants such as sodium bisulfite, ascorbic acid, propyl 3,4,5-trihydroxy benzoate, and the like may be employed. Chelating agents such as citrate, tartrate, or ethylenediaminetetraacetic acid (EDTA) may be used. Other additives useful as stabilizers of corticosteroid prodrugs (e.g., creatinine, polysorbate 80, and the like) may be employed.

Sterile aqueous solutions of compounds of Formula I can be administered to the patent being treated, i.e., a warm blooded mammal, intramuscularly or intravenously or orally. Additionally conventional solid dosage forms of the compounds of Formula I can be administered orally to the patient being treated. For example, capsules, pills, tablets or powders of the compounds of Formula I can be formulated in unit dosage forms incorporating conventional fillers, dispersants, preservatives and lubricants. Also suppositories providing a sustained release of a compound of Formula I can be formulated using conventional inert materials such as biodegradable polymers or synthetic silicones.

The compounds of Formula I are known in the art or are prepared by procedures well known in the art. Illustrative examples of the compounds of Formula I include: 17$\alpha$,21-dihydroxy-4,9(11)pregnadiene-3,20-dione; 6$\alpha$-methylcortisone; 17$\alpha$,21-dihydroxy-6$\alpha$-methylpregna-1,4,9(11)-triene-3,20-dione; and 11-epi-cortisol, and 6$\alpha$-fluoro-17$\alpha$-hydroxy-21-hydroxy-16$\beta$-methylpregna-4,9(11)-diene-3,20-dione.

In Formula I the wavy bond ($\sim$) means the substituent group represented by $R_5$ may be in the alpha or beta position.

Heparin fragment means any part of the heparin compound having substantially the same type of activity as heparin.

EXAMPLE 1

17$\alpha$,21-Dihydroxy-6$\alpha$-methyl-pregn-1,4,9(11)-triene-3,20-dione

A 13.58 g sample of 21-acetoxy-17$\alpha$-hydroxy-6$\alpha$-methylpregna-1,4,9-(11)-triene-3,20-dione in methanol (850 ml) was hydrolyzed with 10% potassium carbonate (34 ml). The reaction mixture was acidified, diluted with water and concentrated to give a gummy precipitate which was dissolved in ethyl acetate. The extract was washed with water and brine, then dried over sodium sulfate and evaporated. Crystallization of the residue from acetone-hexane give the title compound, m.p. 204°-206° C.; one spot by TLC (10% $CH_3OH$—$CHCl_3$).

EXAMPLE 2

(a) Bis-methylenedioxy ketal protected 6$\alpha$-methylcortisone

To a stirred suspension of 70 g (0.187 mol) 6$\alpha$-methylcortisone in 650 ml $CH_2Cl_2$, cooled to 0° C. in an ice/$H_2O$ bath, was added 110 ml concentrated HCl dropwise. To the stirred suspension was added 110 ml of 37% aqueous formaldehyde in three batches at one hour intervals after the cooling bath was removed. The reddish brown mixture was stirred for 18 hours at 25° C. The phases were separated, the aqueous phase was extracted with $CH_2Cl_2$, the combined organic phases were washed with $H_2O$ two times, saturated aqueous $NaHCO_3$, dried ($MgSO_4$) and the solvent removed in vacuo to leave 87.5 g of a brown foam. The material was chromatographed on 2 Kg silica gel, eluting with 1:1 hexane/ethyl acetate to give 25 g product and 6 g of a mixture of product and starting material. Rechromatographing the mixed fractions gave another 5 g of product; yield: 30 g (38%). The material was triturated with $Et_2O$ to give a white powder, m.p. 244°-248° C.

(b) Bis-methylenedioxy protected 6α-methyl cortisone-3-ethyleneketal

A mixture of 20 g (48 mmol) of the compound of Example 2(a), 5.9 g (96 mmol) ethylene glycol, 300 ml benzene and 250 mg p-toluene sulfonic acid was heated at reflux under $N_2$ is a flask fitted with a Dean-Stark trap for 4 hours. The mixture was cooled to 25° C. and washed with 300 ml saturated $NaHCO_3$. The organic phase was dried ($MgSO_4$) and the solvent removed in vacuo to leave 22 g of an oil which crystallized from EtOAc to give 19.5 g (87%) of white solid, m.p. 214°–216° C.

(c) Bis-methylenedioxy protected 6α-methyl-11α-hydrocortisol, 3 ethylene ketal

To a solution of 20 g (43.5 mmol) of the compound of Example 2(b), 92 g (2 mol) absolute ethanol, 200 ml anhydrous $Et_2O$ and 500 ml dioxane (dried over a molecular sieve) in a 5L 3-neck flask fitted with mechanical stirrer and dewer condenser and cooled in a dry ice-/acetone bath was distilled 3L of an anhydrous ammonia. The cooling bath was removed and 15.4 g (2.2 mol) lithium wire was added piecewise over a 2 hour period. The $NH_3$ was allowed to escape overnight. The flask was cooled to 0° C. and 1L ethyl acetate and 1L $H_2O$ was added with stirring until the solids dissolved. The the solution was added 200 ml saturated ammonium chloride. The phases were mixed and separated. The organic phase was dried ($MgSo_4$) and the solvent removed in vacuo to leave 18.5 g of a solid. The material was triturated with $Et_2O$ to give 15.5 g (78%) of a white powder, m.p. 247°–250° C. An analytical sample was crystallized from acetone, m.p. 250°–252° C.

(d) Bis-methylenedioxy protected 6α-methyl-11α-hydrocortisol

A solution of 57 g (0.123 mol) of the compound of Example 2(c), 4 g p-toluene sulfonic acid and 3L acetone was stirred at 25° C. for 24 hours. The acetone was removed in vacuo. The residue dissolved in 2L of $CH_2Cl_2$ and washed with 1L $H_2O$ and 1L saturated $NaHCO_3$. The organic phase was dried ($MgSO_4$) and the solvent removed in vacuo to leave 52 g of a green foam. The material was flash chromatographed in three batches on silica gel (about 200 g) eluting with 1:1 hexane/ethyl acetate to give 20 g (40%) of the title product. A sample of the title compound was crystallized from ethyl acetate, m.p. 203°–204° C.

(e) 11α,17,21-Trihydroxy-6α-methyl-pregn-1,4-diene-3,20-dione, 17,20,21-bis-methylenedioxy A mixture of 7.5 g (18 mmol) of the compound of Example 2(d), 6.13 g (27 mmol) 2,3-dichloro-5,6-dicyanobenzoquinone and 80 ml dioxane (dried over a molecular sieve) was heated at reflux for 18 hours. The mixture was cooled to 25° C. and filtered. The filtrate (black) was flash chromatographed on silica gel (about 200 g), eluting with 1:1 hexane/ethyl acetate to give 6.2 g (83%) of the title compound as a yellow powder after crystallizing from hexane/ethyl acetate, m.p. 255°–258° C.

(f) 11α,17α,21-Trihydroxy-6α-methyl-pregn-4-ene-3,20 dione

A mixture of 3 g (7.18 mmol) of the compound of Example 2(d), and 30 ml of 88% formic acid was heated on a steam bath for 30 minutes. The mixture was cooled to 0° C. and neutralized with 60 ml 45% KOH. The mixture was distributed between 100 ml $H_2O$ and 150 ml $CH_2Cl_2$. The aqueous phase was extracted two times with 100 ml $CH_2Cl_2$. The combined organic phases were dried ($MgSO_4$) and the solvent removed in vacuo to leave 3 g of a brown foam. The resultant formates were hydrolized by stirring the material with 100 ml methanol and 20 ml of 10% $K_2CO_3$ at 25° C. for 30 minutes. The mixture was acidified with 6 ml acetic acid. The methanol was removed in vacuo, the residue take up in $CH_2Cl_2$ (100 ml), washed with $H_2O$ (100 ml), dried ($MgSO_4$) and the solvent removed in vacuo to leave 2.5 g of a brown foam. The material was chromatographed on silica gel (175 g) eluting with 3% methanol, 97% ethyl acetate to give 1.08 g of the title compound as a white foam. An analytical sample was crystallized from ethyl acetate, m.p. 203°–206° C.

(g) 11α,17α,21-Trihydroxy-6α-methyl-pregn-1,4-diene-3,20-dione

A mixture of 2.0 g (4.8 mmol) of the compound of Example 2(e) and 20 ml 60% formic acid was heated at 100° for one hour. The mixture was cooled to 25° C., diluted with 100 ml ethyl acetate and 75 ml $H_2O$ and neutralized with 30 ml 45% KOH. The phases were mixed and separated. The aqueous solution was extracted with ethyl acetate, the combined organic phases were dried ($MgSO_4$) and the solvent removed in vacuo to leave 2 g of a brown foam. The material was stirred with 20 ml methanol and 8 ml 10% aqueous $K_2CO_3$ at 25% for 3 minutes. The methanol was removed in vacuo and the residue distributed between $CH_2Cl_2$ (75 ml) and $H_2O$ (75 ml). The aqueous solution was extracted with $C_2Cl_2$, the combined organic phases were dried ($MgSO_4$) and the solvent removed in vacuo to leave 1.79 g of a glossy solid which was triturated with $Et_2O$ to give 1.5 g of the title compound as a light yellow powder (83%).

EXAMPLE 3

(s) 11α,17,21-Trihydroxy-6α-methyl-pregn-1,4-diene-3,20-dione, 17,21-acetonide

A mixture of 4.8 g (12.8 mmol) of the compound of Example 2(g), 75 ml of 2,2-dimethoxypropane, 30 ml dimethylformamide and 0.12 g p-toluenesulfonic acid was refluxed for 3 hours. The mixture was cooled to 25° C. and distributed between 300 ml ethyl acetate, 150 ml $H_2O$ and 150 ml saturated $NaHCO_3$. The organic phase was dried ($MgSO_4$) and the solvent removed in vacuo to leave 7.2 g crude product as a brown oil. The material was chromatographed on silica gel (175 g) eluting with 1:1 hexane/ethyl acetate to give 2.73 g (52%) of the title compound as a white foam. An analytical sample was crystallized from hexane/ethyl acetate to give a white powder, m.p. 185°–187° C.

(b) 11α-Acetoxy-17αa,21-acetonide-6α-methyl-pregn-1,4-diene-3,20-dione

A mixture of 1.0 g (2.4 mmol) of the compound of Example 3(a), 5 ml acetic anhydride and 20 ml pyridine was stirred at 25° C. for 18 hours. The pyridine was removed in vacuo and the residue distributed between 100 ml ice cold 10% HCl and 100 ml ethyl acetate. The organic phase was dried ($MgSO_4$) and the solvent removed in vacuo to leave 2 g of an oil. The material ws chromatographed on silica gel (175 g) eluting with 70% hexane, 30% ethyl acetate to give 1.0 g of a white foam.

(c) 11α-Acetoxy-17α,21-dihydroxy-6α-methyl-pregn-1,4-diene-3,20-dione

A mixture of 1.0 g (2.2 mmol) of the compound of Example 3(b), 15 ml acetone, 2 ml $H_2O$ and 20 drops of 10% HCl was heated at 45° C. for 3 hours. The mixture was cooled to 25° C. overnight. The solids were collected and washed with cold acetone to leave 0.51 g of the title compound as a white powder. The filtrate was distributed between 75 ml CH$_2$Cl$_2$ and 35 ml H$_2$O. The organic phase was dried (MgSO$_4$) and the solvent removed in vacuo to leave another 0.23 g of the title compound after Et$_2$O trituration, m.p. 275° (dec.).

EXAMPLE 4

| 21-Hydroxy-17α-hydroxy-6α-methylpregna-1,4,9(11)-triene-3,20-dione | 155 mg |
| --- | --- |
| Dilute NaOH to adjust pH to 5.3 | |
| Sterile water for injection to make 1 mlr | |

EXAMPLE 5

| 21-Hydroxy-17α-hydroxy-6α-methylpregna-1,4,9(11)-triene-3,20-dione | 153 mg |
| --- | --- |
| Adipic acid | 7.3 mg |
| Methyl paraben | 1.5 mg |
| Propyl paraben | 0.2 mg |
| NaOH (dilute) to adjust pH to 5.4 | |
| Sterile water for injection to make 1 ml | |

EXAMPLE 6

| 6α-Fluoro-17α,21-dihydroxy-16β-methylenepregna-1,4,9(11)-diene-3,20-dione | 166 mg |
| --- | --- |
| Creatine | 8.0 mg |
| Acetic acid | 4.6 mg |
| Sodium acetate | 2.0 mg |
| Sodium bisulfite | 1.0 mg |
| Disodium edetate | 0.5 mg |
| Benzyl alcohol | 8.8 mg |
| HCl (dilute) or NaOH (dilute) to adjust pH to 5.0 | |
| Water for injection to make 1 ml | |

FORMULA CHART

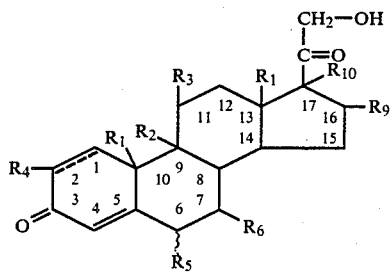

Formula I

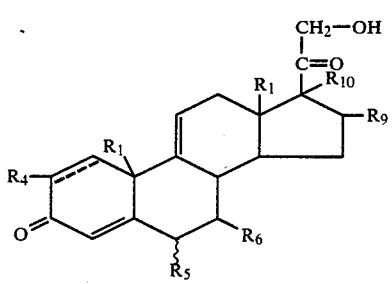

Formula II

-continued
FORMULA CHART

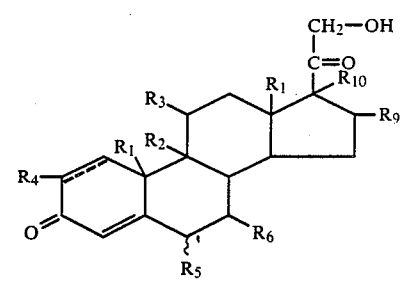

Formula III

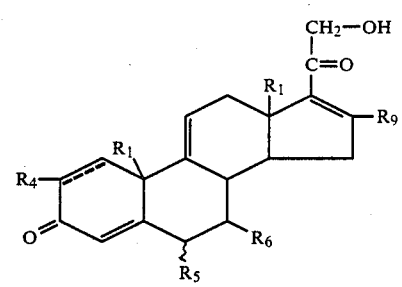

Formula IV

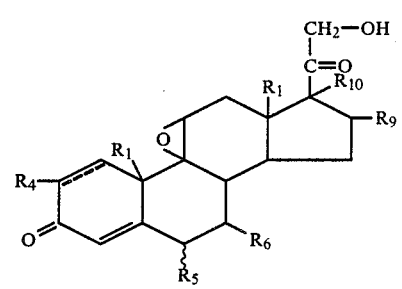

Formula V

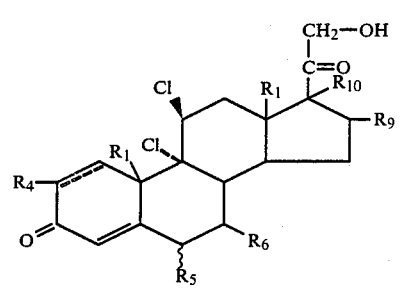

Formula VI

We claim:
1. A method of inhibiting angiogenesis in a warm blooded animal which comprises administering to said animal an anti-angiogenic effective amount of a compound of the formula:

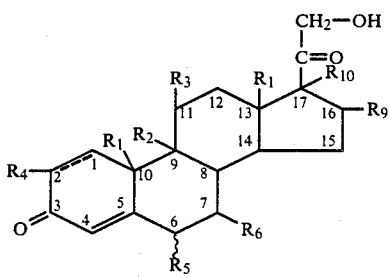

wherein the dotted line between positions C-1 and C-2 means the presence or absence of a double bond; the bond at C-6 denotes α or β;

wherein $R_1$ is $CH_3$ or $-C_2H_5$;

wherein $R_2$ is H, and $R_3$ is in the α-position and is —OH, —O-alkyl($C_1$-$C_{12}$), —OC(=O)alkyl(-$C_1$-$C_{12}$), —OC(=O)aryl, —OC(=O)N(R)$_2$, or —OC(=O)OR$_7$, wherein aryl is furyl, thienyl, pyrrolyl, or pyridyl wherein each of said hetero moiety is optionally substituted with one or two ($C_1$-$C_4$)-alkyl groups or aryl is —(CH$_2$)$_F$-phenyl wherein F is 0 to 2 and wherein the phenyl ring is optionally substituted with one to three groups selected from chlorine, fluorine, bromine, alkyl($C_1$-$C_3$), alkoxy($C_1$-$C_3$), thioalkoxy($C_1$-$C_3$), Cl$_3$C—, F$_3$C—, —NH$_2$ and —NHCOCH$_3$ and wherein R is hydrogen, alkyl(-$C_1$-$C_4$), or phenyl and each R can be the same or different; and wherein $R_7$ is aryl as herein defined or alkyl($C_1$-$C_{12}$); or wherein $R_2$ is α-Cl and $R_3$ is β-Cl; or wherein $R_2$ and $R_3$ taken together are oxygen (—O—) bridging positions C-9 and C-11; or wherein $R_2$ and $R_3$ taken together form a double bond between positions C-9 and C-11;

wherein $R_4$ is H, CH$_3$, Cl or F;

wherein $R_5$ is H, OH, F, Cl, Br, CH$_3$, phenyl, vinyl or allyl;

wherein $R_6$ is H or CH$_3$;

wherein $R_9$ is H, OH, CH$_3$, F or =CH$_2$; and wherein $R_{10}$ is H, OH, CH$_3$ or $R_{10}$ forms a second bond between positions C-16 and C-17; and pharmaceutically acceptable salts thereof; with the proviso that when $R_3$ is α-OH, one of the groups $R_2$, $R_4$, $R_5$, $R_6$, $R_9$ or $R_{10}$ is other than H; coadministered with heparin or a heparin fragment.

2. The method of claim 1 wherein $R_1$ is CH$_3$; $R_4$ is H; $R_5$ is α-CH$_3$, F or H; $R_6$ is H; $R_9$ is H, CH$_3$ or α-OH; and $R_{10}$ is α-H or α-OH.

3. The method of claim 1 wherein $R_4$ is α-F; $R_5$ is α-F, α-Cl or β-OH; $R_9$ is α-OH or α-CH$_3$; and $R_{10}$ is α-OH or α-CH$_3$.

4. The method of claim 1 wherein $R_3$ is alkyl($C_1$-$C_3$); $R_4$ is hydrogen; $R_5$ is H, CH$_3$, OH, F, Cl, or Br; $R_6$ is H or CH$_3$; and $R_9$ is H, α-OH or CH$_3$.

5. The method of claim 4 wherein $R_{10}$ forms a second bond between positions C-16 and C-17.

6. The method of claim 4 wherein $R_{10}$ is α-H or α-OH.

7. The method of claim 6 wherein $R_2$ and $R_3$ taken together form a double bond between positions C-9 and C-11.

8. The method of claim 6 wherein $R_2$ and $R_3$ taken together are oxygen (—O—) bridging positions C-9 and C-11.

9. The method of claim 6 wherein $R_2$ is hydrogen and $R_3$ is —OH, —O-alkyl($C_1$-$C_{12}$), —O-COalkyl($C_1$-$C_{12}$), —O-COaryl, —OCON(R)$_2$ or —OCOR$_7$ wherein aryl, R, and $R_7$ have the meanings defined in claim 1.

* * * * *